United States Patent [19]

Allen et al.

[11] Patent Number: 4,992,202
[45] Date of Patent: Feb. 12, 1991

[54] NON-LINEAR OPTICS

[75] Inventors: Simon Allen; Cheadle Hulme; Paul F. Gordon; John O. Morley, both of Rochdale, all of England

[73] Assignee: Imperial Chemical Industries PLC, London, England

[21] Appl. No.: 420,719

[22] Filed: Oct. 13, 1989

Related U.S. Application Data

[63] Continuation of Ser. No. 10,611, Feb. 4, 1987, abandoned.

[30] Foreign Application Priority Data

Feb. 4, 1986 [GB] United Kingdom ................ 8602708

[51] Int. Cl.$^5$ .................................. C09K 19/54
[52] U.S. Cl. .................. 252/299.5; 252/582; 252/587; 350/350 R; 350/96.12; 548/379
[58] Field of Search .............. 252/299.5, 600, 582, 252/589, 587; 548/379; 350/350 R, 354, 1.1, 3.64, 96.12

[56] References Cited

U.S. PATENT DOCUMENTS

| | | | |
|---|---|---|---|
| 4,090,782 | 5/1978 | Bredfeldt et al. | 350/357 |
| 4,093,358 | 6/1978 | Shattack et al. | 350/357 |
| 4,174,393 | 11/1979 | Van Daalen et al. | 548/379 |
| 4,692,266 | 9/1987 | Costa et al. | 252/600 |

FOREIGN PATENT DOCUMENTS 1331228 9/1973 United Kingdom .

OTHER PUBLICATIONS

Hall, S. R. et al., J. Cryst. Growth 79 (1986) 745.
CA 88:5885u.
March, J. Adv. Org. Chem. 3rd ed., Wiley & Sons, New York, 1985, pp. 242-244.
Davy Dov, Bl. et al. Optics & Spec, vol. 30(3) 274, 1971.
Docherty, V. J. et al, J.C.S. Faraday Trans 2, 81, 1179, 1985.
Williams, D. J., Angew Chem Int Ed Engl. 23, 690, 1984.
CA 88:5885u (1978).
CA 106:129619v (1987).
CA 94:155856y (1981).
CA 87:53279a (1977).

*Primary Examiner*—John S. Maples
*Assistant Examiner*—Richard Treanor
*Attorney, Agent, or Firm*—Cushman, Darby & Cushman

[57] ABSTRACT

Optical elements having non-linear optical properties comprising a compound of the formula:

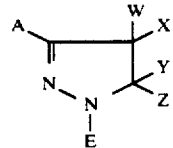

wherein
E is an electron donor
A is an electron acceptor;
and W, X, Y & Z are each independently H or any group capable of attachment to the pyrazolyl ring; in which the molecules of the compound are aligned so that the element has a net non-centrosymmetry, a method for their preparation, optical devices comprising such elements, and compounds of formula I.

7 Claims, 1 Drawing Sheet

NON-LINEAR OPTICS

This is a continuation of application No. 07/010,611, filed Feb. 4, 1987, which was abandoned upon the filing hereof.

This specification describes an invention relating to a non-linear optical (NLO) element and devices containing such elements.

According to the present invention there is provided an optical element having non-linear optical properties, hereinafter referred to as the "NLO element", comprising a compound of the formula:

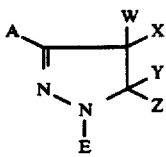   I wherein
A is an electron acceptor;
E is a group comprising a long aliphatic chain;
and W, X, Y and Z are each independently H or a substituent, in which the molecules of the NLO compound are aligned so that the the element has a net non-centrosymmetry, which alignment is herein after referred to as "ordered".

The group, E, preferably comprises an aliphatic chain containing at least 10 carbon atoms and more preferably from 12 to 25 carbon atoms, E', which is preferably an alkyl or alka(poly)enyl chain.

One or more chains represented by E' may be attached directly to the 1—N atom of the pyrazoline ring or through a linking group, L, comprising a system of conjugated double and single bonds between E' and the pyrazoline ring, such as phenylene, naphthylene or alk(poly)enylene. The group E can thus be represented by the formula:

—(L)$_l$—(E')$_m$   II wherein
L and E' are as hereinbefore defined;
l is 0 or 1;
and m is an integer from 1 to 3.
Examples of such groups are 4-nonylphenyl, 4-dodecylphenyl, 4-octadecylphenyl, octdecenyl and octadecadienyl.

The electron acceptor, A, comprises one or more atoms or groups which readily accept electronic charge, A', preferably containing nitrogen and oxygen atoms, carbon and oxygen atoms, sulphur and oxygen atoms and/or halogen atoms. Specific examples of suitable electron acceptors are —NO, —NO$_2$, —CN, —NC, halogen, especially F, Cl or Br, —CHO, —COOH, —COT, —COOT, —CH=NT, —CONTV, —N=NT and —C=CH, in which T and V independently represent H, alkyl, alkenyl, heteroaryl or aryl, especially phenyl and preferably phenyl substituted by one or more electron withdrawing groups, such as —NO, —NO$_2$, —CHO, —COOT, —CONTV and —CN. Especially preferred examples of A' are —NO$_2$, —CHO, —COOT, —COT, —CONTV and —CN. The electron acceptor, A, preferably also comprises a group containing conjugated double and single bonds, L, through which it is attached to the 3-C atom of the pyrazoline ring. It is preferred that L represents a phenylene, naphthylene or alka(poly)enylene, which may carry other substituents, including further groups represented by A'. Thus the electron acceptor, A, can conveniently be represented by the formula:

—(L)$_l$—(A')$_m$   III wherein L, A', l and m are as hereinbefore defined. Examples of such groups are 4-cyanophenyl and 2,4-dinitrophenyl.

The groups represented by W, X, Y and Z are isolated from the conjugated electron pathway between the the group, E, and the electron acceptor, A, and, therefore, do not significantly interfere with the electro-optical properties of the molecule. They can represent any group(s) capable of attachment to the pyrazoline ring but, for convenience of preparation, are preferably hydrogen.

Examples of suitable pyrazolines of Formula I are 1-(4-nonylphenyl)-3-(4-nitrophenyl)-pyrazoline and 1-(4-octadecylphenyl)-3-(4-nitrophenyl)-pyrazoline.

The molecules of the NLO compound are non-centrosymmetric by virtue of their polarisation along an axis through the the group, E, the pyrazoline ring and the electron acceptor, A. A molecule of the compound can therefore be represented as a vector directed along this axis from the group, E, towards the electron acceptor, A. A material, such as an optical element, comprising the NLO compound, either alone or in conjunction with other substances, in which the molecules of the NLO compound are "ordered" (i.e. not randomly oriented so that the sum of the individual molecular vectors is zero) will have an overall non-centrosymmetry and thus be adapted for non-linear optical applications.

The NLO element may comprise the NLO compound of Formula I alone or it may be medium comprising a physical or chemical combination of the NLO compound of Formula I with other compounds which may or may not have NLO properties.

The NLO element may comprise (i) a bulk sample of the NLO compound, such as a single crystal prepared by crystallisation from solution, from the melt, by vapour phase transport or by other known methods of crystallisation, or (ii) an chemically inert medium containing the NLO compound, such as a liquid crystal material, in which the NLO compound may be ordered by the application of a d.c. electric field. The ability of the NLO compound to form an "ordered" crystal is believed to be promoted by the presence in the molecule of a chiral atom which promotes the formation of crystals in which the molecules are "ordered" so that the bulk sample is non-centrosymmetric. It is therefore preferred that an NLO compound for use in the preparation of a single crystal NLO element contains one or more chiral atoms.

However, the NLO compound of Formula I is adapted for the formation of thin films and the NLO element preferably comprises a thin film of the NLO compound on a transparent or reflecting substrate, for use in waveguiding geometries well known in this field of work. The film may itself be used as a waveguide, to maximise non-linear optical interactions, or may be used as a non-linear optically-active overcoat to an active or passive waveguide.

The film may be formed by epitaxial crystal growth or by crystallisation of the material in a narrow cavity between two substrates but is preferably formed by Langmuir-Blodgett deposition onto a transparent or reflecting substrate.

The NLO element may be employed in optical devices which exhibit second-order non linear effects such as second harmonic generation, frequency mixing or the d.c. electro-optical effect.

Examples of non-linear optical effects using an NLO element in accordance with the present invention, in the form of a bulk sample, for example a single crystal, of the NLO compound, include:

(1) Second Harmonic Generation: A laser beam of given frequency, incident on one face of an NLO element comprising an "ordered" single-crystal of the NLO compound, at an angle parallel to the so-called "phase-matching" direction, causes the emission from the element of a coherent beam of laser radiation, at twice the frequency of the incident beam, in a direction substantially parallel to the incident beam.

(2) Electro-optical Amplitude Modulation. A polarised laser beam is directed so that it passes through a birefrequent NLO element, comprising an "ordered" crystal of the NLO compound, at an angle such that the plane of polarisation is rotated, by an angle Q, on passing through the crystal and then through a polarising medium (the 'analyzer') which transmits a proportion of the beam corresponding to Q. An electric field, applied across the NLO element causes a change in the birefringence (the "d.c. electro-optic effect") of the element and a consequent change in the angle of rotation of the polarized output beam, to Q'. The proportion of the beam transmitted by the analyzer now corresponds to Q'.

Where the NLO element comprises a thin film of the NLO compound on a substrate this preferably comprises at least two monolayers of the NLO compound, in which the molecules in both layers are "ordered", and more preferably all the molecules are aligned in the same manner and such an optical element comprises a second aspect of the present invention.

By "aligned in the same manner" is meant that the vectors along the axes of polarization in the molecules are substantially parallel and in the same sense.

It is not essential that the monolayers of the NLO compound are adjacent and it can be advantageous to separate the monolayers with intervening layers of other materials. Where the two monolayers of the NLO compound are adjacent it is preferred that the groups represented by E in the molecules forming one monolayer will be adjacent to the electron acceptors, A, in the molecules forming the adjacent monolayer ("head to tail" array).

Where the substrate is transparent at the wavelength of incident radiation it may be in the form of an optical waveguide on the outer surface of which the NLO compound is deposited. With this form of element an optical signal passing along the waveguide interacts with the superficial coating of the NLO compound, via the evanescent wave which extends into this coating, and gives rise to non-linear optical effects. Examples of suitable substances for a substrate in the form of a waveguide are glass, lithium niobate and silicon nitride on oxidized silicon.

Alternatively, a transparent substrate may be in the form of a plate or disc on one, or both, surfaces of which a coating of the NLO compound can be formed in discrete monolayers. With this form of element a non-linear optical effect may be obtained by transverse illumination of the substrate and film(s). Suitable substrates for such an optical element include glass, silica and polymethylmethacrylate (PMMA).

Where the substrate is reflecting it conveniently has a plane reflecting surface on which a superficial coating of the present NLO compound, in discrete monolayers, may be formed so that the optical signal passes through the coating immediately before and after contact with the reflecting surface. Example of suitable materials for the reflecting substrate are aluminium, silver, or aluminium or silver films deposited on a support substrate such as glass, silica, quartz or PMMA. With this form of optical element it is possible to attain efficient non-linear processes by exciting the so called "surface plasmon" modes reported in the literature [Stegman et al., Appl.-Phys.Lett. 41 (10) 906, 1982; Sand et al., Appl. Optics 21 (22) 3993, 1982].

The optical element in the form of a thin layer of the NLO compound on a substrate may be prepared by a Langmuir-Blodgett technique and according to a third aspect of the invention there is provided a method for the preparation of an optical element having non-linear optical properties which comprises passing a surface of a transparent or reflecting substrate into and out of a Langmuir trough containing a liquid carrying a superficial monomolecular layer of a compound of Formula I (the NLO compound). Where the layers of the NLO compound are not adjacent intervening layers may be formed by passing the substrate into the liquid through a surface carrying a superficial layer of the NLO compound and out of the liquid through another surface carrying a superfical layer of a different compound, or vice versa.

The liquid, hereinafter referred to as the sub-phase, is preferably an aqueous medium and the mono-molecular layer or layers are maintained in the normal manner by adjustment of the surface area with movable dams.

The optical element comprising a thin layer of the NLO compound on a substrate is adapted for the production second order non-linear optical effects in a number of ways in various optical devices.

According to a fourth aspect of the present invention there is provided an optical device comprising a non-linear optical element in accordance with the second aspect of the present invention.

An example of an optical device in accordance with the fourth aspect of the present invention, in which the optical element comprises a substrate in the form of a transparent waveguide having an intimate coating formed by multiple layers of the present NLO compound, consists of an oxidized silicon plate having a first superficial (lower) layer of silicon nitride to form a superficial plane waveguide and a second superficial (upper) layer comprising discrete monolayers of the NLO compound. In operation, a first optical signal is passed through the waveguide, (in the plane of the waveguide) and interacts with the coating, by way of the evanescent wave which extends into the coating. This interaction generates a second optical signal, at the second harmonic frequency with respect to the first optical signal, which can be detected in the combined optical signal leaving the waveguide.

BRIEF DESCRIPTION OF THE DRAWINGS

Another device in accordance with the present invention is described in relation to FIGS. 1 and 2 of the accompanying drawings, in which.

Figure 1:
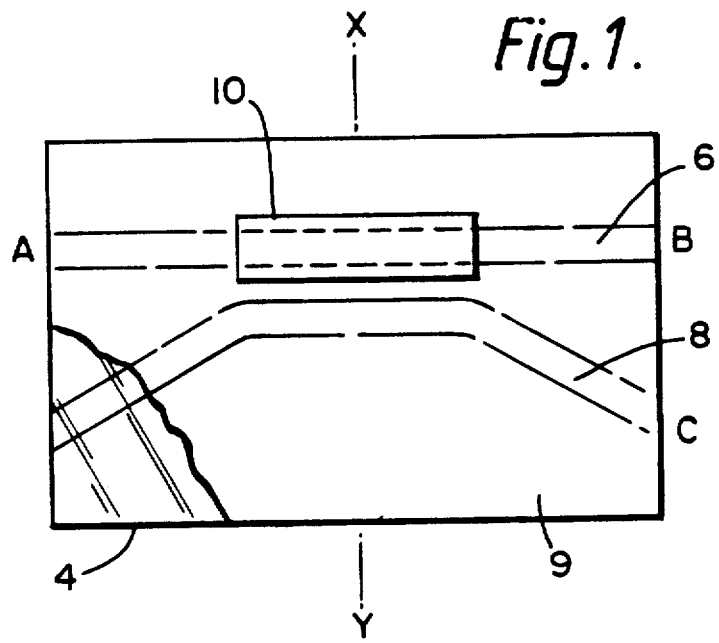
FIG. 1 is a plan view and FIG. 2 is a cross-section on the line X-Y in FIG. 1. In the device the optical element comprises a glass substrate, 4, in the upper surface region, 5, of which are two transparent stripe waveguides, 6 and 8, formed in the desired pattern by the well-known ion exchange or ion bombardment techniques. The stripe waveguides are positioned to run closely parallel over the central part of their length during which they are separated by a distance of a few micrometers (typically 2-5 $\mu$m). The whole surface of the substrate, 4, is coated with a film, 9, of discrete monolayers of the NLO compound. A pair of electrodes, 10, 12, connected to a power source, not shown, is arranged with one electrode, 10, above and the other, 12, below one of the stripe waveguide, 6. In operation an optical signal is passed through the first waveguide, 6, from A to B and a voltage is applied across the electrodes. This alters the refractive index of the coating, due to the d. c. electro-optic (Pockels) effect, and thus the propagation constant of the first waveguide, 6. By suitable adjustment of the applied voltage the propagation constant of the first waveguide, 6, can be arranged so that the optical signal passing through this waveguide, 6, is coupled into the second waveguide, 8, and produces a second optical signal emerging from the device at C.
Figure 2:
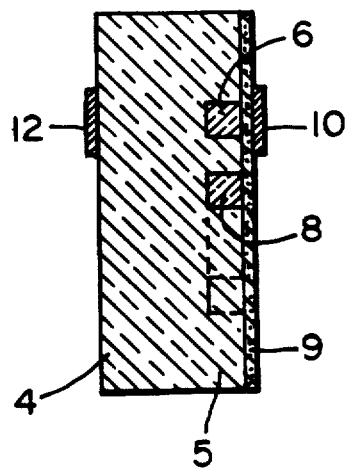

The optical element of the second aspect of the present invention may be used in other known forms of optical device incorporating an optical element by replacing the conventional NLO compound used therein, e.g. lithium niobate, with the NLO compound of Formula I.

The compounds of formula I are believed to be novel and as such form a fifth aspect of the present invention.

In addition to exemplary and preferred groups E' within group E within the compounds of formula I, suitable groups E' also include groups —OT, —ST, —NTV and PTV in which T represents an aliphatic chain containing at least 10 and preferably 12 to 25 carbon atoms, and V is independently H or a group as defined for T.

Examples of such E' include dodecoxy, dodecylthio and dodecylamino.

In addition to suitable pyrazolines of formula I listed hereinbefore, suitable pyrazolines also include:
1-(4-dodecylaminophenyl)-3-(4-nitrophenyl)-pyrazoline(1),
1-(4-dodecoxyphenyl)-3-(4-nitrophenyl)pyrazoline,
1-(4-dodecylthiophenyl)-3-(4-nitrophenyl)pyrazoline,
1-(4-dodecylamino-1-naphthyl)-3-(4-nitrophenyl)-pyrazoline(1),
1-(4-dodecylaminophenyl)-3-(4-cyanophenyl)pyrazoline,
1-(4-dodecylaminophenyl)-3-(4-isocyanophenyl)-pyrazoline,
1-(4-dodecylaminophenyl)-3-(4-fluorophenyl)pyrazoline,
1-(4-dodecylaminophenyl)-3-(4-formylphenyl)pyrazoline,
1-(4-dodecylphenyl)-3-(4-nitrophenyl)pyrazoline,
1-(4-octadec-1'-enylphenyl)-3-(4-nitrophenyl)pyrazoline,
1-(4-octadeca-1', 3'-dienylphenyl)-3-(4-nitrophenyl)-pyrazoline,
1-(4-dodecylphenyl)-3-(4-methoxycarbonylphenyl)-pyrazoline,
1-(4-dodecylphenyl)-3-(4-acetylphenyl)pyrazoline,
1-(4-dodecylphenyl)-3-(4-dimethylamidophenyl)-pyrazoline, and
1-(4-dodecylphenyl)-3-(4-phenyliminomethylphenyl)-pyrazoline.

The compounds of formula I may be synthesized analogously to or are readily and routinely derivable from known pyrazolines. For example it is often convenient to react two compounds of general form A–G and E–J where A and E are as hereinbefore defined and G and J react to form the pyrazoline nucleus.

Syntheses of this type are illustrated in the Examples hereinafter, as are other aspects of the invention.

In the following Examples parts and percentages are by weight unless otherwise indicated.

EXAMPLE 1

(a) 1-(4-dodecylaminophenyl)-3-(4-nitrophenyl)-pyrazoline(1)

A mixture of N,N-dimethyl-N-4-nitrobenzoyl ethylammonium chloride (18 g), 4-dodecylaminophenylhydrazine hydrochloride (D1) (12 g) and sodium carbonate (21 g) in ethanol (200 ml) is boiled for 30 min.

The mixture is cooled to room temperature, and the precipitated product (1) is filtered off washed well with water and dried at 50° C. (14 g).

A sample is purified by recrystallization from toluene/hexane.

The starting materials (including (D1)) are known compounds.

The compounds of formula I listed hereinbefore are prepared analogously (including 1-(4-octadecylphenyl)-3-(4-nitrophenyl)-pyrazoline(2)) are prepared analogously.

The calculated $\beta$ values of compounds (1) and (2) are as follows:

EXAMPLE 2

A dipping bath is prepared by slow dripping 10 $\mu$l of a solution of compound (2) as prepared in Example 1 in chloroform (1mg/ml) from a micro-syringe onto the surface of an aqueous sub-phase having a surface area of 1000 CM$^2$ in a Langmuir trough. The surface pressure is adjusted to 15 mN/m by movement of the barriers and maintained at this level throughout the dipping process.

A pre-cleaned, thin glass plate is successively dipped into and withdrawn from the sub-phase at a speed of 3 mm/min. Deposition of a monolayer of (2) occurs substantially only during withdrawal of the substrate from the sub-phase and dipping is continued until a film comprising 20 monolayers of (2) are deposited on the part of both of the parallel faces of the plate which passes through the monolayer of (2). All the molecules of (2) in the film are aligned substantially parallel with the vectors in the same sense, i.e. the molecules in the separate monolayers are in "head to tail" array. The film of (2) is removed from one plane surface of the plate and the resulting optical element comprises a glass substrate coated on one plane surface with multiple monolayers of (2).

Elements comprising compounds of formula I listed hereinbefore are prepared analogously to that above, in particular elements comprising compound (1).

EXAMPLE 3

The optical element described in Example 2 is used in the following manner to demonstrate the noncentrosymmetric nature of the applied film.

A beam of light from, a Nd:YAG pulsed laser (wavelength: 1.06 $\mu$m) is passed transversely through the plate and the film of (2). The intensity of light at the second harmonic (wavelength: 0.53 $\mu$m) generated during passage through the element is detected and measured with a photodiode. The measurement is used to calculate the non-linear optical coefficient of the NLO compound and n is the refractive index of the NLO compound.

Other elements referred to in Example 2 are tested analogously.

EXAMPLE 4

The second order molecular hyperpolarisability coefficient (B) of the compounds of formula I are determined routinely using the well-known EFISH (Electric Field Induced Second Harmonic) experiment described in J. Chem. Phys., 63, 2666 (1975) on a number of solutions of the compounds at various concentrations to determine the macroscopic susceptibility (see also J. Chem. Phys., 67 446 (1979) and Phys, Rev Lett. 8 21 (1962) and using routinely determined refractive indices and dielectric constants.

What is claimed is:

1. An optical element having non-linear optical properties comprising a compound selected from the group consisting of:

1-(4-nonylphenyl)-3-(4-nitrophenyl)-pyrazoline;
1-(4-octadecylphenyl)-3-(4-nitrophenyl)-pyrazoline;
1-(4-dodecylaminophenyl)-3-(4-nitrophenyl)pyrazoline;
1-(4-dodecylthiophenyl)-3-(4-nitrophenyl)pyrazoline;
1-(4-dodecylamino-1-naphthyl)-3-(4-nitrophenyl)-pyrazoline;
1-(4-dodecylaminophenyl)-3-(4-cyanophenyl)pyrazoline;
1-(4-dodecylaminophenyl)-3-(4-isocyanophenyl)-pyrazoline;
1-(4-dodecylaminophenyl)-3-(4-fluorophenyl)pyrazoline;
1-(4-dodecylaminophenyl)-3-(4-formylphenyl)pyrazoline;
1-(4-dodecylphenyl)-3-(4-nitrophenyl)pyrazoline;
1-(4-octadec-1-enylphenyl)-3-(4-nitrophenyl)pyrazoline;
1-(4-octadec-1',3'-dienylphenyl)-3-(4-nitrophenyl)-pyrazoline;
1-(4-dodecylphenyl)-3-(4-methoxycarbonylphenyl)-pyrazoline;
1-(4-dodecylphenyl)-3-(4-acetylphenyl)pyrazoline;
1-(4-dodecylphenyl)-3-(4-dimethylamidophenyl)-pyrazoline; and
1-(4-dodecylphenyl)-3-(4-phenyliminomethylphenyl)-pyrazoline;

the molecules of said compound being aligned so that the element has a net non-centrosymmetry.

2. An optical element according to claim 1 comprising a single crystal of said compound or a chemically inert liquid crystal material containing said compound aligned in said liquid crystal material by the application of a d.c. electric field.

3. An optical element according to claim 1 wherein the element comprises a thin film of the compound on a substrate.

4. An optical element according to claim 3 wherein the element comprises at least two monolayers of the compound in each of which monolayers the molecules of the compound are aligned as defined.

5. An optical element according to claim 4 wherein all the molecules of the compound are aligned such that the vectors along the axis of polarization in the molecules are substantially parallel and in the same sense.

6. In an optical device including a non-linear optical element, the modification wherein said element is an element as defined in claim 1.

7. An optical element according to claim 1 wherein said compound is 1-(4-dodecylaminophenyl)-3-(4-nitrophenyl)pyrazoline.

* * * * *